Figure 1:
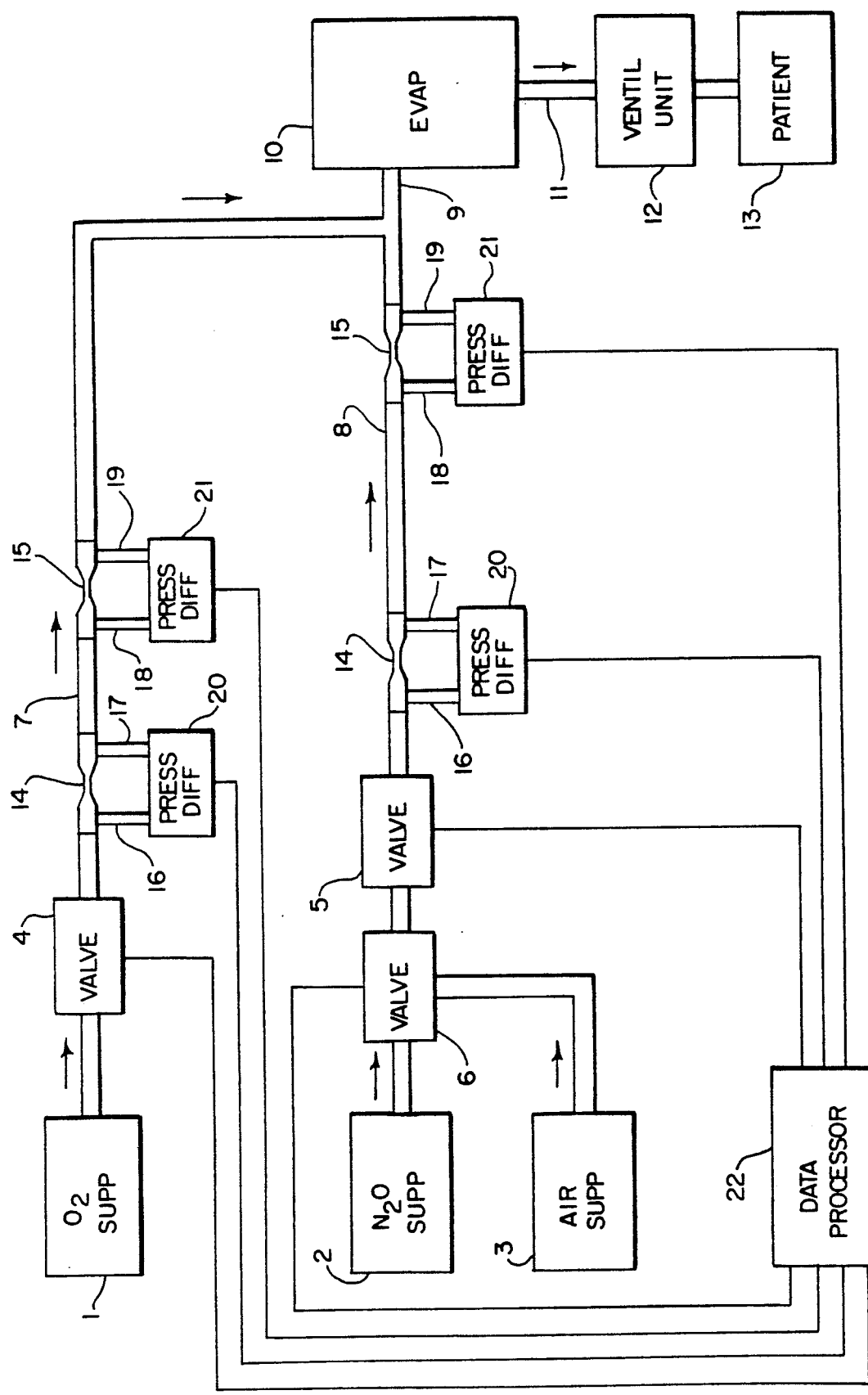

United States Patent [19]

Heinonen

[11] Patent Number: 5,161,406
[45] Date of Patent: Nov. 10, 1992

[54] IDENTIFICATION METHOD FOR A GAS FLOW AND ITS DISTURBANCES

[75] Inventor: Erkki Heinonen, Helsinki, Finland
[73] Assignee: Instrumentarium Corp., Finland
[21] Appl. No.: 652,658
[22] Filed: Feb. 6, 1991
[30] Foreign Application Priority Data Feb. 8, 1990 [FI] Finland ................. 900639

[51] Int. Cl.⁵ .................................................. G01N 9/32
[52] U.S. Cl. ........................................ 73/23.2; 73/31.040
[58] Field of Search ................... 73/23.2, 31.04, 54, 73/861.04, 861.63

[56] References Cited

U.S. PATENT DOCUMENTS

| | | | |
|---|---|---|---|
| 2,984,105 | 5/1961 | Nagel et al. | 73/861.04 X |
| 3,086,386 | 4/1963 | Kapff | 73/23.2 X |
| 3,505,855 | 4/1970 | Rolland | 73/54 X |
| 4,576,043 | 3/1986 | Nguyen | 73/861.04 X |
| 4,662,219 | 5/1987 | Nguyen | 73/861.04 X |
| 4,836,032 | 6/1989 | Redus et al. | 73/861.04 |
| 4,856,344 | 8/1989 | Hunt | 73/861.63 X |
| 4,941,345 | 7/1990 | Altemark et al. | 73/23.2 X |

FOREIGN PATENT DOCUMENTS

| | | | |
|---|---|---|---|
| 439731 | 8/1974 | U.S.S.R. | 73/31.04 |
| 356322 | 9/1931 | United Kingdom . | |
| 1304430 | 1/1973 | United Kingdom . | |

Primary Examiner—Hezron E. Williams
Assistant Examiner—Joseph W. Roskos
Attorney, Agent, or Firm—Andrus, Sceales, Starke & Sawall

[57] ABSTRACT

The invention relates to a method and an apparatus for the identification of a gas flow or its disturbances. A gas flowing in a gas pipe is allowed to pass through at least two flow-restricting elements in series, the pressure differences of a flowing gas being measured over said elements and effecting the identification by means of such measured pressure differences.

15 Claims, 3 Drawing Sheets

IDENTIFICATION METHOD FOR A GAS FLOW AND ITS DISTURBANCES

The present invention relates to a method and apparatus for the identification of a gas flow and its disturbances. Measuring results can be used for the identification of gases, and particularly those respired by a patient, such as for example oxygen. The invention is particularly well applicable in an effort to make sure that some particular gas is present so as to recognize the tendencies to bring some other gas into the same space. Measuring results can be further used to discover the failure of a flow meter and leaks in a flow line.

A typical anaesthesia machine includes a gas mixer, an evaporator and a ventilator. One basic function of the apparatus is to take care of the oxygen delivery to a patient during surgery. The factors forming a threat to oxygen supply include disturbances in the oxygen supply pressure, malfunctions, coupling faults in oxygen supply systems, tubing leaks and disconnections of tubes.

Efforts have been made to resolve the above problems by means of a "fail-safe" valve which shuts off other gas supplies whenever the oxygen pressure falls too low. However, this does not respond to a flow failure caused by a malfunction or a clogging. This has been resolved by incorporating in the above system a flow measurement, whereby a decrease of oxygen flow also decreases the flow of other gases. Even this system is not capable of preventing an erroneous substitution of some other gas for oxygen, a tubing leak or disconnections of tubes. At the present technical level, this can only be verified by means of an oxygen-content indicator. However, such a device is expensive and requires regular maintenance and must always be separately installed and activated and, thus, it is not always available.

An object of this invention is to eliminate the above problems. One object of the invention is to provide a method and apparatus for the identification of a gas flowing in a gas piping and particularly to provide a method capable of confirming the presence of some certain gas, such as for example oxygen, whereby the erraneous couplings of unintended gases to a gas pipeline can be discovered in time. The invention serves e.g. as a permanent part of a gas mixer used in anaesthesia and, thus, is always available for use. A further object of the invention is to discover the damaging of a flow meter and any leak in a flow line. Another object of the invention is to provide an apparatus compatible with the above objects, which is simple in design and economical in price.

The characterizing features of a method of the invention are set forth in the annexed claims.

The basic feature of the invention is that a gas line issuing from a gas container is provided with at least two flow-restricting elements, the pressure difference being measured over each such element. From either side of the flow-restricting element extends a measuring channel to a measuring element, which is thus preferably a pressure-difference measuring element and which element compares the pressure prevailing on either side of the flow-restricting element. Depending on a particular case, a further object is the mutual comparison of pressure differences detected by both pressure-difference measuring elements either as such or as converted by means of calibration information. On the basis of this comparison, the obtained results are used to identify a gas flowing in the pipeline or a gas leak or any damage to the flow meter. Thus, a clogging e.g. in one or the other of the flow-restricting elements is detected and, thus, it can be said that the flow-restricting elements are self-controlling. In order to identify a gas, the flow-restricting elements must be of different types, i.e. the flow having passed therethrough must have profiles different from each other. On the other hand, the type of flow-restricting elements bears no significance in the detection of a clogging or a leak.

There are currently available primarily two types of flow-restricting elements or flow restrictors, namely a laminar and a turbulent restrictor. In a laminar restrictor, the flow keeps running linearly, the flow profile being parabolical, i.e. the flow advances more rapidly in the central part of a pipe than in the lateral parts of a pipe. A gas flowing through a turbulent restrictor keeps running in a turbulent pattern, the flow profile being linear, i.e. the flow advances simultaneously in the middle and in the lateral parts of a pipe. Due to changes occuring in the flow, the pressure difference measured over a restrictor depends on the type of a restrictor.

The pressure difference over a laminar restrictor is proportional to the viscosity of a flow and the flow of the gas. The pressure difference measured over a turbulent restrictor is proportional to the square of the flow and inversely proportional to the density of a flowing gas. Thus, if pressure signals are calibrated into flows, the ratio between the flows of a laminar and a turbulent restrictor is as follows: flow (lamin.)/flow (turb.)$= \kappa/(\eta \times \sqrt{\rho})$ wherein K is a restriction ratio, $\eta$ is viscosity and $\rho$ is density. When the flows are calibrated for a certain gas, e.g. oxygen, whereby the laminar flow is equal to the turbulent flow, the result is $$\kappa = \eta_{o2} \times \sqrt{\rho_{o2}}$$

If other than oxygen is flowing in a channel calibrated for oxygen, the ratio of flows will be: flow (lamin.)/flow (turb.)$=(\eta_{o2} \times \sqrt{\rho_{o2}})/(\eta \times \sqrt{\rho})$ wherein $\eta$ is viscosity of a flowing gas and $\rho$ is its density.

If the flow-restricting elements are of different types, i.e. one is a laminar and the other is a turbulent restrictor, the pressure-difference readings provided by the measuring elements can be used to identify a gas flowing in a pipeline providing that said gas consists of a compound having a ratio of viscosity and density which differs sufficiently from the corresponding ratio of other possible gases. This gas identification method is of a particular interest whenever it is known which gases are available during the course of some operation and which gas is desired to flow along that particular gas line which is provided with flow-restricting elements. Thus, the invention is excellent in identifying a fresh gas administered to a patient in anaesthesia. Such gases include nitrogen oxidule, air and oxygen. In this case, especially, various flow-restricting elements could be used for the identification of oxygen administered to a patient in order to make sure that a patient definitely receives the gas most important in view of surviving and to detect a hazardous situation even in the case that a gas line, which should have oxygen connected therewith, would in fact have some other gas connected therewith.

For an automatic identification it is necessary to store in the memory of a processor the data on the flow-pressure relationship of flow-restricting elements, i.e. the calibration data for a particular gas whose presence should be verified. During the course of identification, the processor compares the pressure differences detected from various pressure-restricting elements to the calibration readings stored in the memory. In the case of an incorrect connection and as a gas is flowing through the flow-restricting elements in a gas line, whereby the pressure differences detected by a processor are not in agreement with the readings' stored in the memory, the processor automatically triggers e.g. an alarm and possibly shuts off the flow of a gas in question. Although its presence is beneficial, the processor is not necessary but pressure differences can also be directly monitored from pressure-difference measuring elements and the results can be manually compared to calibration readings.

It is self-evident that the identification of a gas can be effected in a variety of ways by working further on the measured pressure differences. When comparing the pressure differences as such, the relationship thereof depends both on the overall flow and the ratio of viscosity and density. Thus, the calibration data of known gases must be calibrated according to a flow in question. Since the pressure difference created over a turbulent restrictor is proportional to the square of a flow and with a laminar restrictor directly to a flow, the identification can be simplified by linearizing the flow dependencies of a pressure difference. Thus, the flow dependency of the quantities to be compared is identical and the ratio of these quantities can be directly compared to the calibration data of the gases. Naturally, one or the other or both of the measured pressure differences can be used to calculate a certain reference value which is then compared to the calibration data. It is also possible to first carry out a calibration which produces a ratio still dependent on a flow, which ratio can be compared to the calibration data calibrated to match a particular flow in question.

When using two identically calibrated flow-restricting elements or a laminar and a turbulent restrictor or two laminar restrictors or two turbulent restrictors in a common gas line in successive order, the pressure differences over both restrictors should remain unchanged, i.e. the flows should remain the same provided that there are no problems within the zone between restrictors. This phenomenon can indeed be utilized since, if the flows passing through the restrictors differ from each other, information is provided on a clogging occuring in one or the other restrictor or on gas leak taking place in the pipeline. In this case, it would be beneficial to place the flow-restricting elements at the forward and terminal ends of a gas line, so that possible variations in the flow would be detected over a range as wide as possible.

Figure 2:
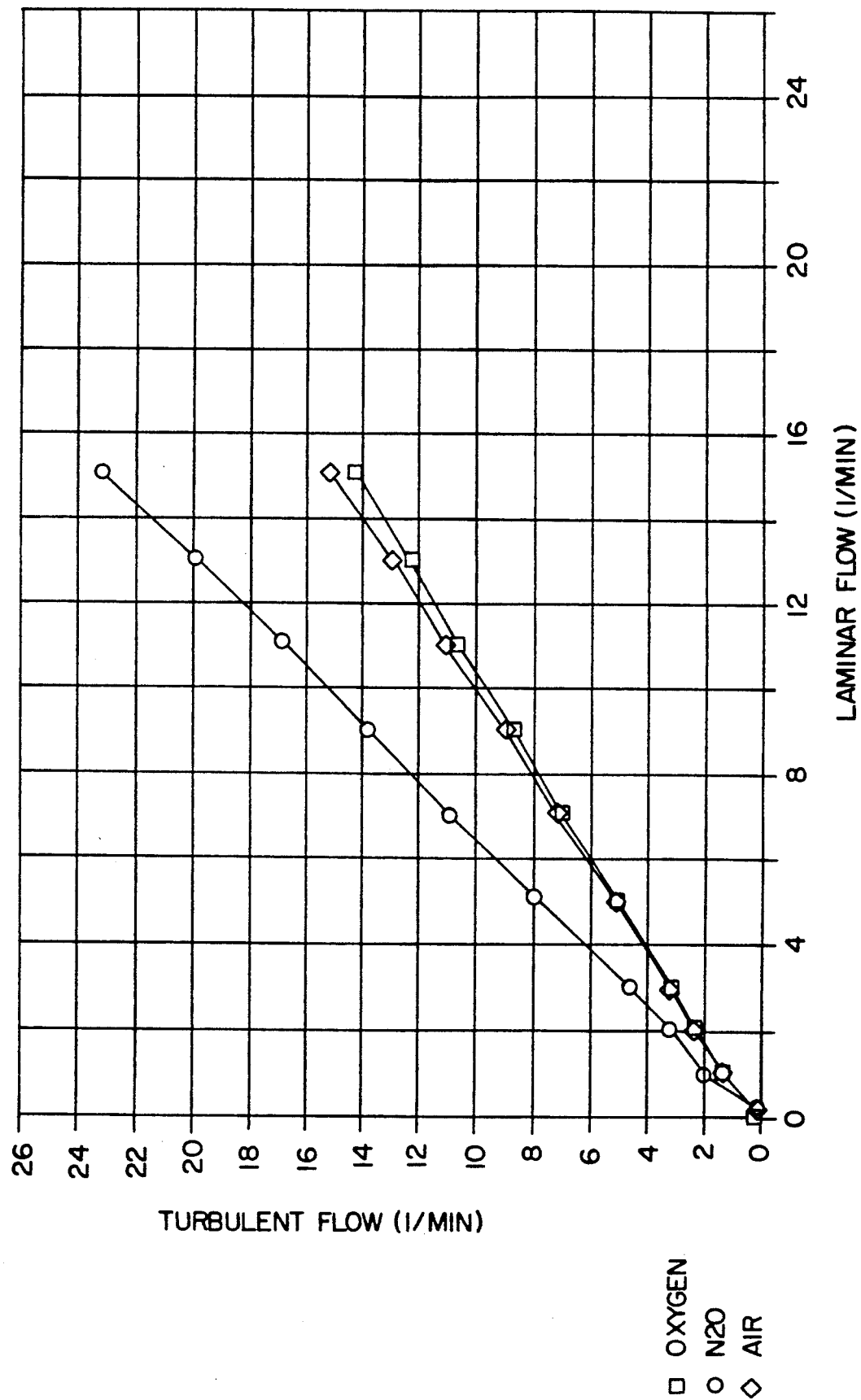
Figure 3:
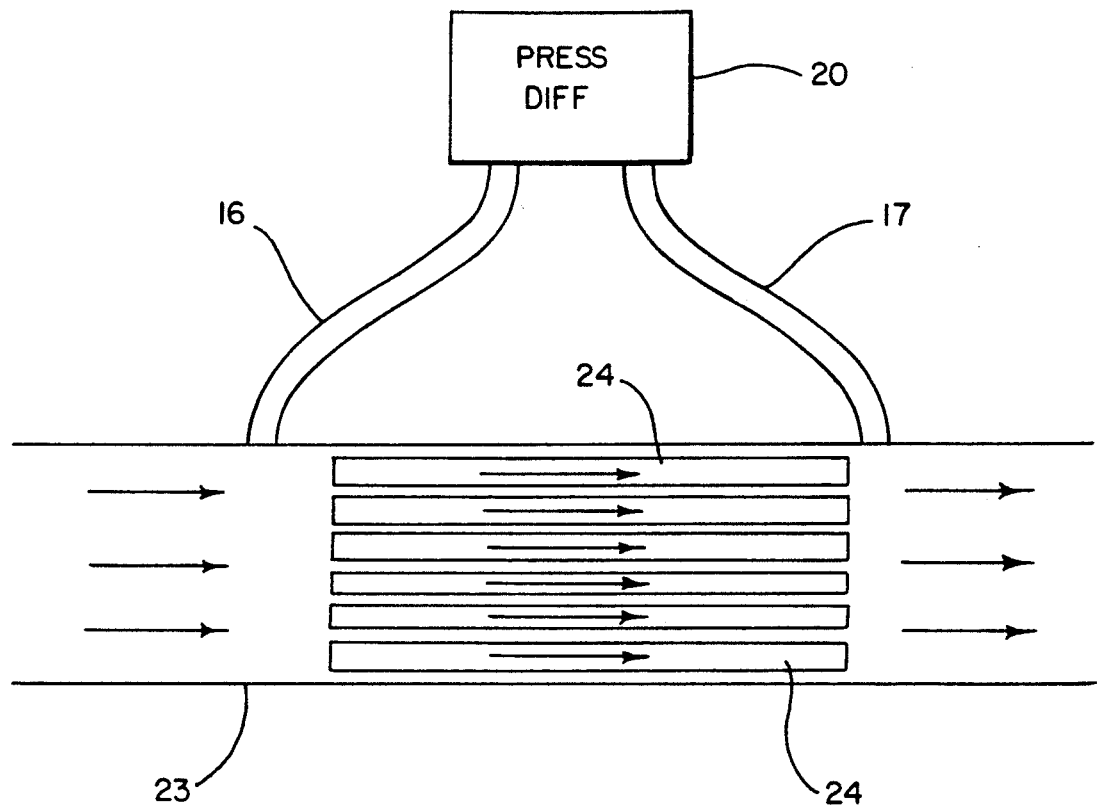
Figure 4:
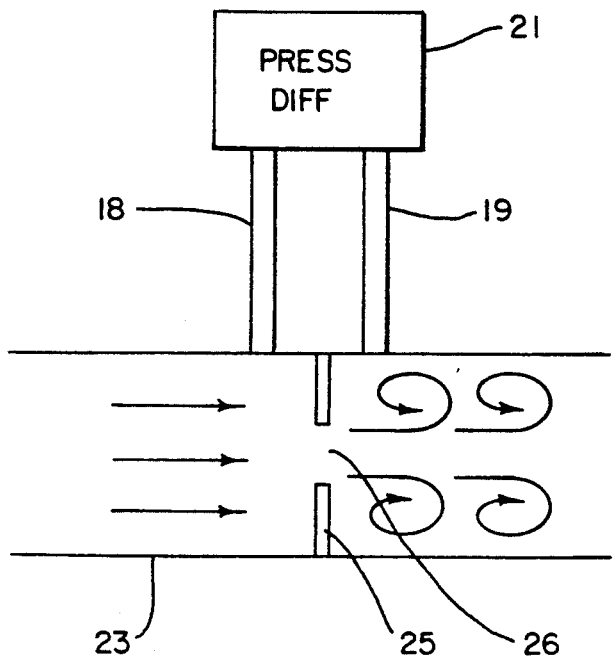

The invention will now be described in more detail with reference made to the accompanying drawings, in which FIG. 1 shows a schematic view revealing an apparatus of the invention, said apparatus being operable in applying a method of the invention, FIG. 2 illustrates the flows measured by a turbulent and laminar flow-restricting element for various gases after calibrating the elements identical to each other by means of air, FIG. 3 shows a longitudinal section of one possible flow-restricting element operable in an apparatus and a method of the invention, FIG. 4 shows a longitudinal section of another possible flow-restricting element operable in an apparatus and a method of the invention.

FIG. 1 shows primarily a schematic view of an apparatus that can be used in anaethetizing a patient. In the apparatus, the elements controlling gas flows from containers 1, 2 and 3 comprise valves 4 and 5, which are preferably needle valves controlled by a stepping motor. The fresh gas comprises e.g. a mixture of either oxygen and nitrogen oxidule or alternatively oxygen and air. Oxygen is contained in container 1 while container 2 contains nitrogen oxidule and container 3 has air. A valve 6, which is preferably a two-way magnetic valve, is used to select one or the other of the gases in containers 2 or 3.

Pipes 7 and 8 leading from the containers join each other and this combined flow of gases is carried along a pipe to an evaporator 10, in which an anaesthetic is admixed in the gas flow. The flow continues further along a pipe 11 by way of a ventilation unit 12 to a patient 13.

A pipe leading from container 1 is provided in successive order with two flow-restricting elements 14 and 15.

One of the flow-restricting elements is laminar and the other is turbulent. The successive order thereof in pipe 7 is not significant. From either side of these elements lead measuring channels 16, 17, 18 and 19 to measuring elements 20 and 21, which are preferably pressure difference measuring elements.

The gas flows from container 1 along pipe 7 to flow-restricting element 14, which issues a signal by way of flow channels 16 and 17 to measuring element 20 which in turn reports a detected pressure difference to a processor 22. From flow-restricting element 14 the gas continues to travel along pipe 7 to the second flow-restricting element 15 for measuring a pressure difference by means of a measuring element 21. The information about a measured pressure difference is delivered to processor 22 which compares to each other the results received from measuring elements 20 and 21, one of which is coupled with a laminar flow-restricting element and the other with a turbulent flow-restricting element. On the basis of pressure differences measured over different, i.e. laminar and turbulent flow-restricting elements, a processor calculates by means of calibration data stored in the memory a flow rate through each flow-restricting element. If the flow rate are equal, the processor interprets everything O.K., i.e. the flowing gas is what it should be and the flow meter is not damaged and no leaks are detected, either. On the other hand, if the flow rates are different from each other, this indicates that the line contains other than a desired gas or there is either a clogging or a leak in the gas line.

FIG. 2 illustrates oxygen, air and nitrogen oxidule flow rates measured by means of a laminar and turbulent flow-restricting element. In this exemplary case, the ratio of a laminar and a turbulent flow with these gases is 1,05 (oxygen), 1,00 (air) and 0,65 (nitrogen oxidule). Thus, in order to make a processor capable of identifying the gases, it is necessary to have pressure difference readings provided by two different flow-restricting elements from one and the same gas flow.

If, in the case of FIG. 1, said pipe 7 should carry through two different flow-restricting elements 14 and 15 anything other than oxygen, said processor 22 would detect on the basis of pressure difference readings obtained from measuring elements 20 and 21 that a wrong gas is coupled with pipe 7 and would report this information to the operator of the apparatus e.g. in the form of an alarm. The processor can also be programmed to shut off valve 4 for stopping the delivery of a wrong gas into pipe 7.

The block diagram of FIG. 1 shows also a possibility of detecting a leak occurring between two successive flow-restricting elements or a damage to the flow meter. A pipe 8 leading from containers 2 and 3 is provided with two identical flow-restricting elements 14 and 15. Thus, both can be either laminar or turbulent. From both ends thereof, the same way as pointed out above, lead measuring channels 16, 17, 18 and 19 to measuring elements 20 and 21 which deliver the data on a pressure difference to a processor 22. If the flow rates calculated by the processor on the basis of detected pressure differences and calibration data are different from each other, this indicates that the flow meter is out of order or there is a gas leak in the gas line creating a hazard to the safety of a patient. If the similar type flow-restricting elements used in the identification of a fault are also completely identical in their restriction characteristics, the calibration data is not needed at all but, instead, leaks and cloggings can be detected simply by comparing the detected pressure differences to each other.

In order to identify gas flow disturbances, these flow-restricting elements 14 and 15 should preferably be located as far away from each other as possible in one and the same gas line in order to find the disturbances over a sufficiently wide range. Even in this case, if the flow rates er, in certain cases, just the pressure differences differ from each other, the processor produces an alarm signal. Thus, the identification of a gas is not possible when using two identical flow-restricting elements.

In anaesthesia, the functions of processor 22 preferably include also the adjustment of a desired oxygen-/laughing gas mixture ratio or oxygen/air mixture ratio and an overall gas flow by means of valves 4, 5 and 6.

FIG. 3 illustrates a longitudinal section of a conventional laminar flow-restricting element which is constructed by dividing the inner space of an actual gas pipe 23 into a plurality of small tubes 24, the flow remaining laminar in each of these tubes over a measuring range in question.

FIG. 4, on the other hand, illustrates a longitudinal section of a conventional turbulent flow-restricting element which comprises a plate 25, extending peripherally around a gas pipe 23 and being set against the flow as well as having an aperture 26 in the middle for discharging the gas arriving along said pipe 23. Another conventional solution is a reverse construction, i.e. a flow-stopping plate is located in the middle of a pipe for discharging the gas through a space between the plate and the walls of a pipe. After passing around a barrier set in its path, a previously laminar flow tends to keep running in a turbulent pattern, as shown in FIG. 4.

FIGS. 3 and 4 illustrate also measuring elements 20 and 21 for detecting a pressure difference, said elements receiving the signals along measuring channels 16, 17, 18 and 19 from either side of the flow-restricting elements. Depending on the factors thereof affecting the nature of a gas flow, said measuring elements show varying pressure difference readings even though a flow arriving at the different types of flow-restricting elements would be originally similar. It is self-evident that the pressure difference can be adjusted in different types of flow-restricting elements by varying the size of a flow-passing aperture.

The drawings describe just one possible solution and various other possibilities exist within the scope of the annexed claims. Thus, the invention which relates to a gas identification method and to an apparatus for carrying out said method is not limited to anaesthetic application but, instead, it can be used in other applications in which the ratio of the viscosity and density of gases are sufficiently different from each other. Also the identification method for cloggings and leaks as well as an apparatus for use therein can be used in other applications and it does not depend on the flow profile of the restrictors.

In addition to those illustrated in FIGS. 3 and 4, there are several different types of flow-restricting elements that are prior known and can be used when applying this invention. However, the most essential aspect in the identification of a gas is the use of such flow-restricting elements which change the flow profile of a gas in the ways different from each other.

In a pressure difference measuring effected over the flow-restricting elements, the number of measuring channels leading to the measuring elements can be for example three instead of four, since a pressure signal arriving at different measuring elements can be picked up from a single spot for each measuring element along a single common measuring channel. Thus, the number of measuring channels is not significant as long as a pressure difference can be measured over each flow-restricting element.

I claim:

1. A method of identifying a single-phase gas that flows through a gas pipe, comprising:
   flowing a gaseous stream through a first flow-restricting element;
   measuring a first pressure difference across said first flow-restricting element as said gaseous stream passes through said first flow-restricting element;
   flowing substantially the entire gaseous stream across a second flow-restricting element, said second flow-restricting element being connected in series with said first flow-restricting element;
   measuring a second pressure difference across said second flow-restricting element as said gaseous stream passes through said second flow-restricting element; and
   identifying said gas using said first pressure difference and said second pressure difference.

2. The method of claim 1, wherein said first flow-restricting element and said second flow-restricting element have different flow profiles.

3. The method of claim 1, where said first flow-restricting element is a turbulent flow-restricting element, and wherein said second flow-restricting element is a laminar flow-restricting element.

4. The method of claim 1, wherein said identifying step includes:
   converting said first pressure difference and said second pressure difference into first and second flow rates respectively using pressure-flow calibration data; and
   comparing said first flow rate with said second flow rate to identify said gas.

5. The method of claim 4, further comprising:
   providing said pressure-flow calibration data for a gas sought to be identified.

6. The method of claim 4, further comprising:
indicating that said gaseous stream is flowing properly if said first flow rate is substantially equal to said second flow rate.

7. The method of claim 1, further comprising:
sensing the pressure of said gaseous stream at a first end and at a second end of said first flow-restricting element;
generating a first pressure signal corresponding to said pressure at said first end, and generating a second pressure signal corresponding to said pressure at said second end;
transmitting said first and second pressure signals to at least three measuring channels of a measuring element;
calculating a pressure difference signal from said first pressure signal and said second pressure signal using said measuring element, and transmitting said pressure difference signal to a processor; and
processing said pressure difference signal using said processor to identify said gas.

8. The method of claim 7, wherein said measuring element is a pressure difference measuring element.

9. A method of identifying a single-phase gas that flows through a gas pipe, comprising:
flowing a gaseous stream through a first flow-restricting element;
measuring a first pressure difference across said first flow-restricting element as said gaseous stream passes through said first flow-restricting element;
flowing substantially the entire gaseous stream across a second flow-restricting element, said second flow-restricting element being connected in series with said first flow-restricting element;
measuring a second pressure difference across said second flow-restricting element as said gaseous stream passes through said second flow-restricting element; and
identifying said gas using said first pressure difference, said second pressure difference and calibration data.

10. A method of identifying a single-phase gas that flows through a gas pipe, comprising:
flowing a gaseous stream through a first flow-restricting element;
measuring a first pressure difference across said first flow-restricting element as said gaseous stream passes through said first flow-restricting element;
flowing substantially the entire gaseous stream across a second flow-restricting element, said second flow-restricting element being connected in series with said first flow-restricting element;
measuring a second pressure difference across said second flow-restricting element as said gaseous stream passes through said second flow-restricting element;
converting said first pressure difference and said second pressure difference into first and second flow rates respectively using pressure-flow calibration data; and
comparing said first flow rate with said second flow rate to identify said gas.

11. An apparatus that identifies a single-phase gas that flows in a pipe, comprising:
a first flow-restricting element;
means for flowing a gaseous stream through said first flow-restricting element;
means for measuring a first pressure difference across said first flow-restricting element as said gaseous stream flows through said first flow-restricting element;
a second flow-restricting element connected in series with said first flow-restricting element such that substantially the entire gaseous stream also passes through said second flow-restricting element;
means for measuring a second pressure difference across said second flow-restricting element as said gaseous stream flows through said second flow-restricting element; and
means for identifying said gas using said first pressure difference and said second pressure difference.

12. The apparatus of claim 11, wherein said first flow-restricting element and said second flow-restricting element have different flow profiles.

13. The apparatus of claim 11, wherein said first flow-restricting element is a turbulent flow-restricting element, and wherein said second flow-restricting element is a laminar flow-restricting element.

14. The apparatus of claim 11, wherein said means for measuring said first pressure difference is a pressure difference measuring element.

15. The apparatus of claim 11, wherein said identifying means includes a processor.

* * * * *